US011471599B2

(12) United States Patent
Säll et al.

(10) Patent No.: US 11,471,599 B2
(45) Date of Patent: Oct. 18, 2022

(54) MEDICAMENT DELIVERY DEVICE

(71) Applicant: Carebay Europe Ltd., Sliema (MT)

(72) Inventors: Daniel Säll, Segeltorp (SE); Rasmus Renstad, Stockholm (SE); Nikolaj Hautaviita, Bro (SE)

(73) Assignee: SHL MEDICAL AG, Zug (CH)

( * ) Notice: Subject to any disclaimer, the term of this patent is extended or adjusted under 35 U.S.C. 154(b) by 283 days.

(21) Appl. No.: 15/777,580

(22) PCT Filed: Oct. 26, 2016

(86) PCT No.: PCT/EP2016/075797
§ 371 (c)(1),
(2) Date: May 18, 2018

(87) PCT Pub. No.: WO2017/084842
PCT Pub. Date: May 26, 2017

(65) Prior Publication Data
US 2021/0196891 A1 Jul. 1, 2021

(30) Foreign Application Priority Data

Nov. 19, 2015 (EP) .................................. 15195279

(51) Int. Cl.
A61M 5/20 (2006.01)
(52) U.S. Cl.
CPC ... *A61M 5/2033* (2013.01); *A61M 2205/3576* (2013.01); *A61M 2205/502* (2013.01);
(Continued)
(58) Field of Classification Search
CPC .......... A61M 5/2033; A61M 2205/502; A61M 2205/583; A61M 2205/3576
(Continued)

(56) References Cited

U.S. PATENT DOCUMENTS 6,202,642 B1    3/2001  McKinnon
2004/0054326 A1*  3/2004  Hommann ................ F16F 1/10
                                                       604/131
(Continued)

FOREIGN PATENT DOCUMENTS

WO    2010052275 A2    5/2010
WO    2012001493 A2    1/2012
(Continued)

*Primary Examiner* — Bhisma Mehta
*Assistant Examiner* — Nidah Hussain
(74) *Attorney, Agent, or Firm* — McDonnell Boehnen Hulbert & Berghoff LLP

(57) ABSTRACT

The present invention relates to a medicament delivery device comprising a housing (10), which housing is arranged to accommodate a medicament container (20); a power unit (88) comprising: a drive force element (98), an actuation unit (90, 102) operably connected to said drive force element (98); which actuation unit (90, 102) is movable, upon activation of said drive force element (98), for expelling a dose of medicament from said medicament container (20); a monitoring unit (130) provided with an electrical power source (140) for operating said monitoring unit (130). The invention is characterised in that the medicament delivery device further comprises an activation element (160) operably connected to said actuation unit (90, 102), to said monitoring unit (130) and to said electrical power source (140), wherein said activation element (160) is arranged to allow connection between said electrical power source (140) and said monitoring unit (130) when said actuation unit (98, 102) is moved.

20 Claims, 14 Drawing Sheets

(52) U.S. Cl.
CPC . *A61M 2205/581* (2013.01); *A61M 2205/582* (2013.01); *A61M 2205/583* (2013.01); *A61M 2205/8206* (2013.01)

(58) Field of Classification Search
USPC .......................................................... 604/134
See application file for complete search history.

(56) References Cited

U.S. PATENT DOCUMENTS

| | | | |
|---|---|---|---|
| 2010/0211005 A1 | 8/2010 | Edwards et al. | |
| 2014/0171879 A1* | 6/2014 | Butler | G01D 5/25 604/218 |
| 2016/0361503 A1* | 12/2016 | Bendek | A61M 5/46 |
| 2018/0221582 A1* | 8/2018 | Klemm | A61M 5/31553 |

FOREIGN PATENT DOCUMENTS

| | | |
|---|---|---|
| WO | 2015076745 A1 | 5/2015 |
| WO | 2015132234 A1 | 9/2015 |

* cited by examiner

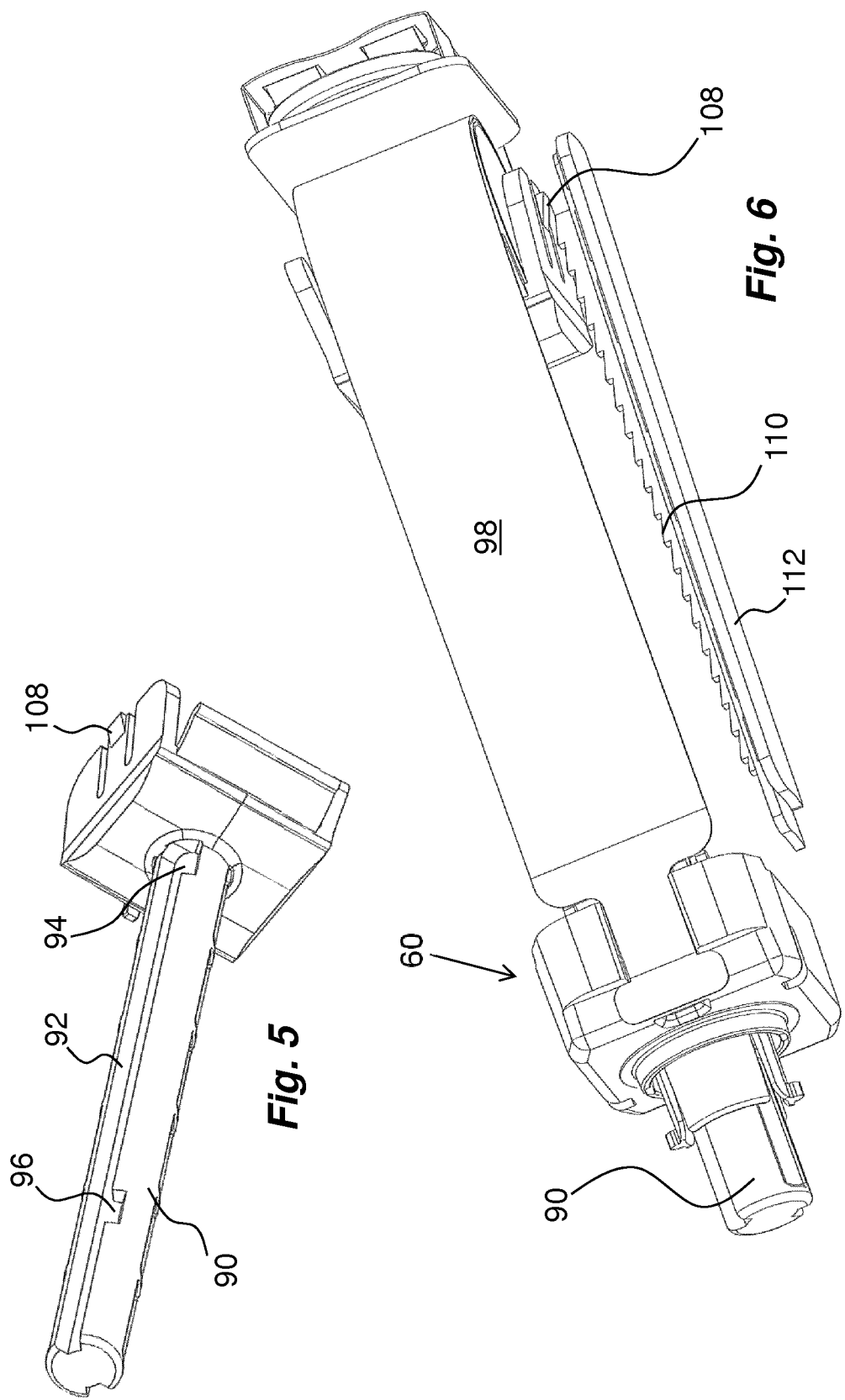

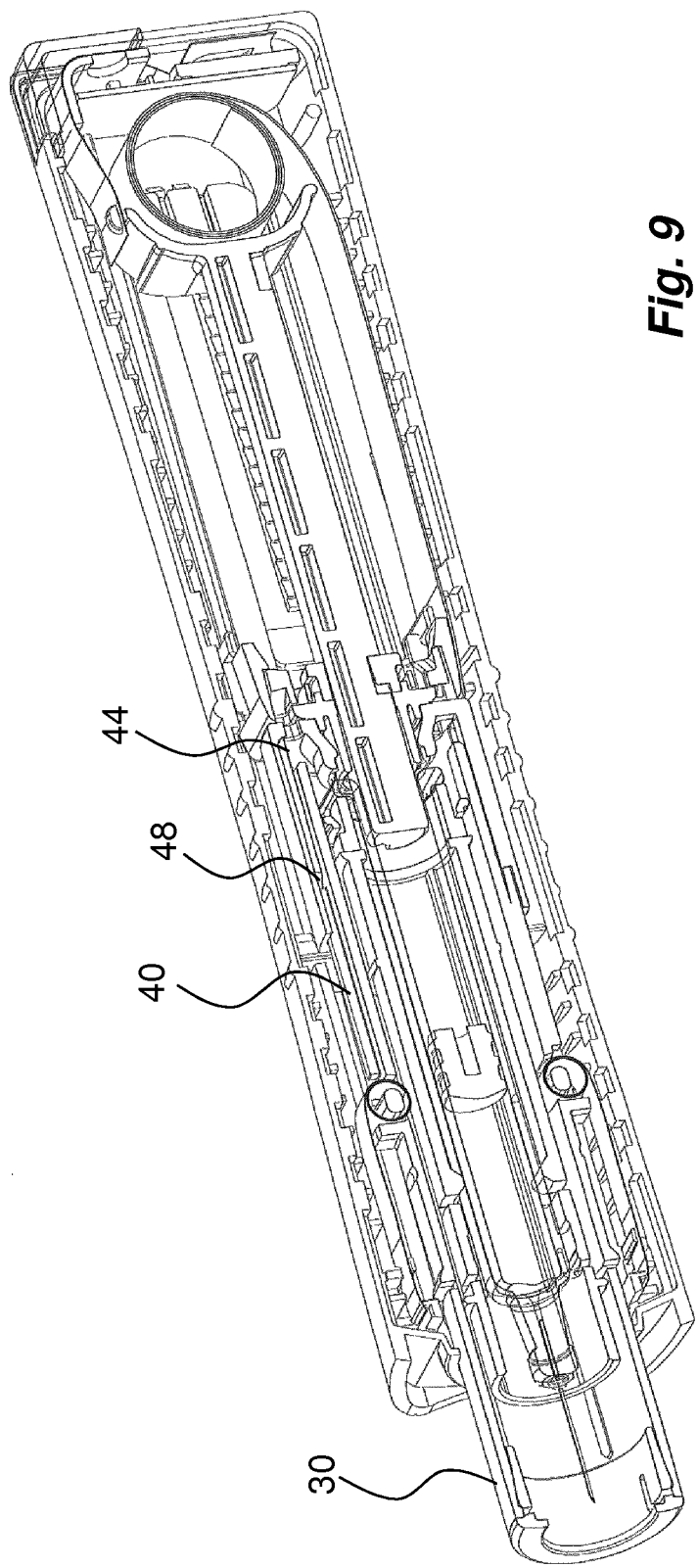

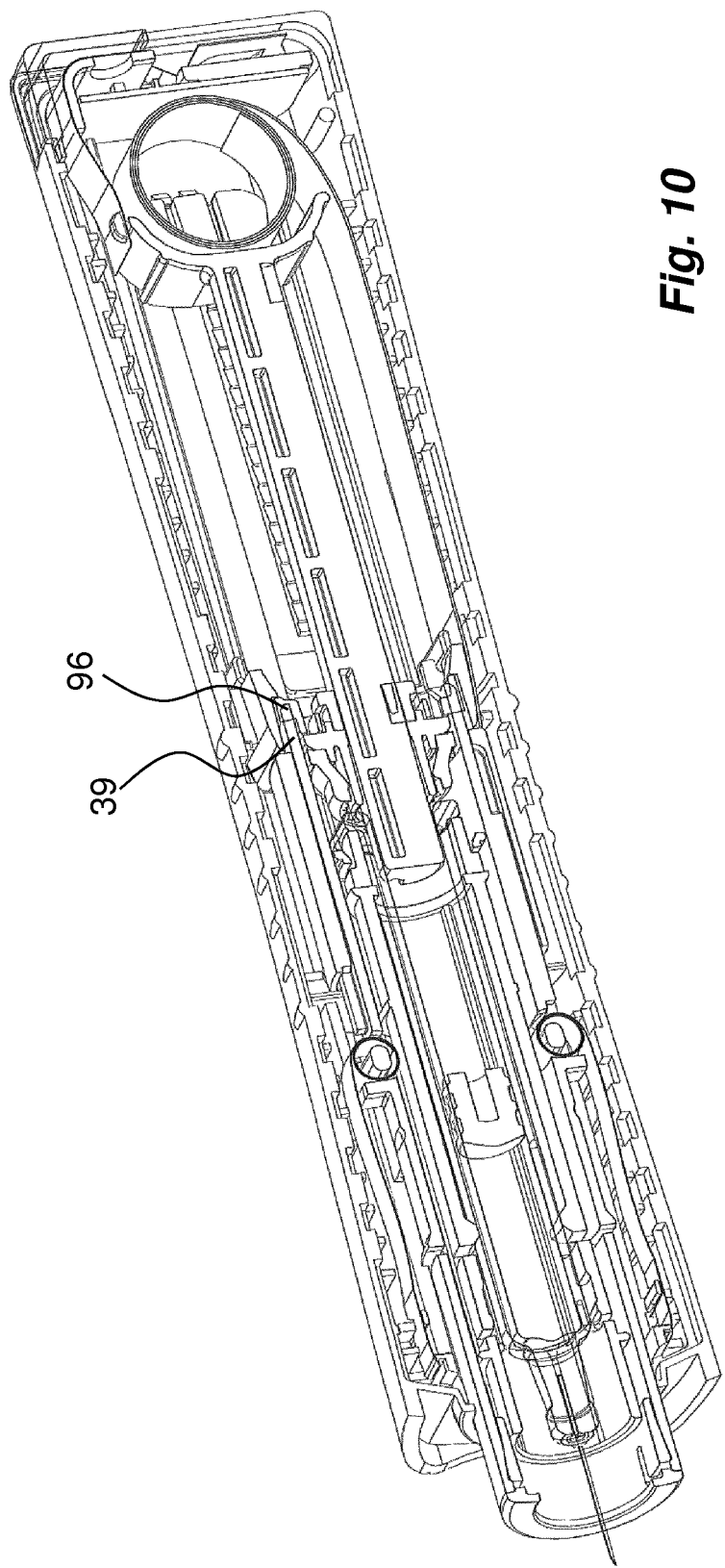

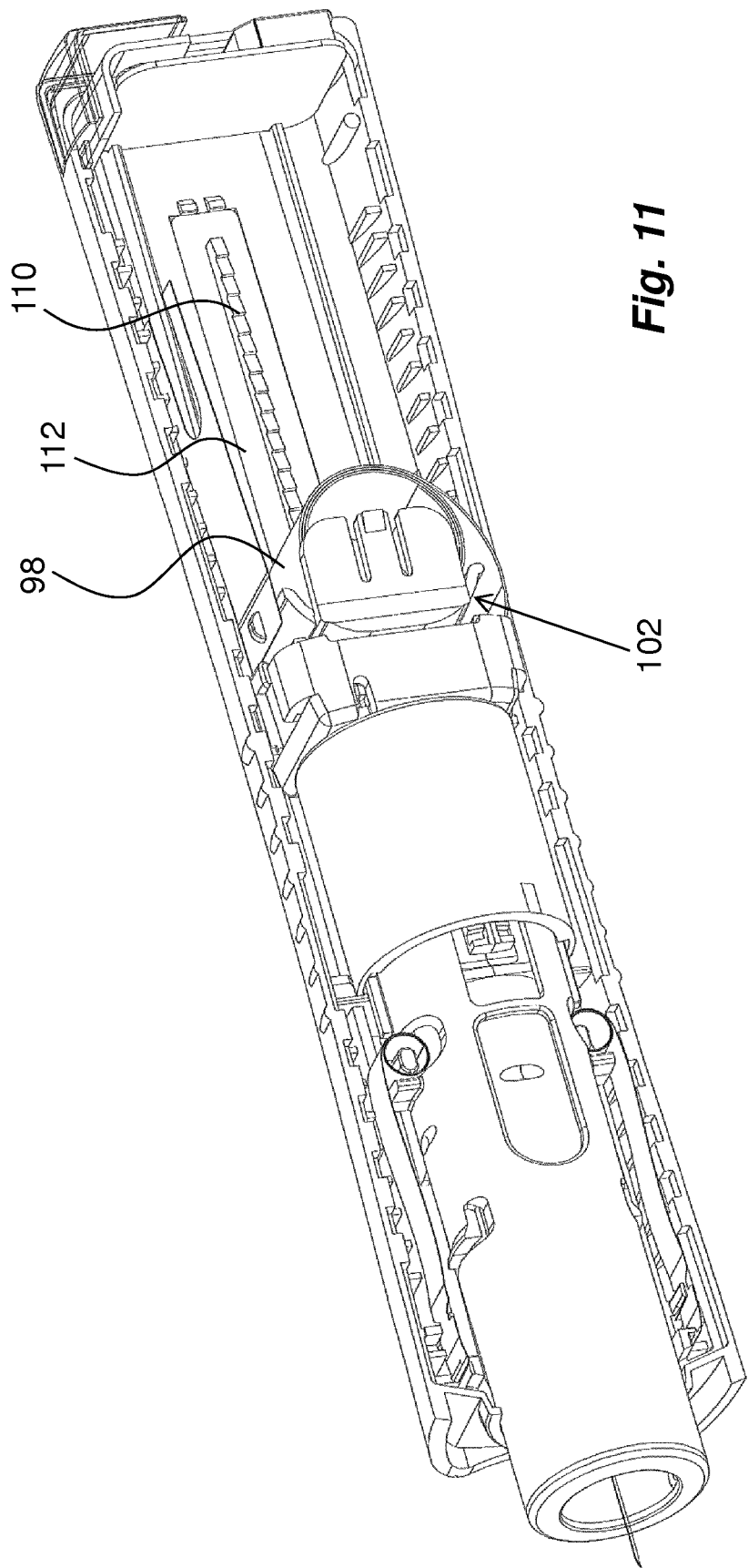

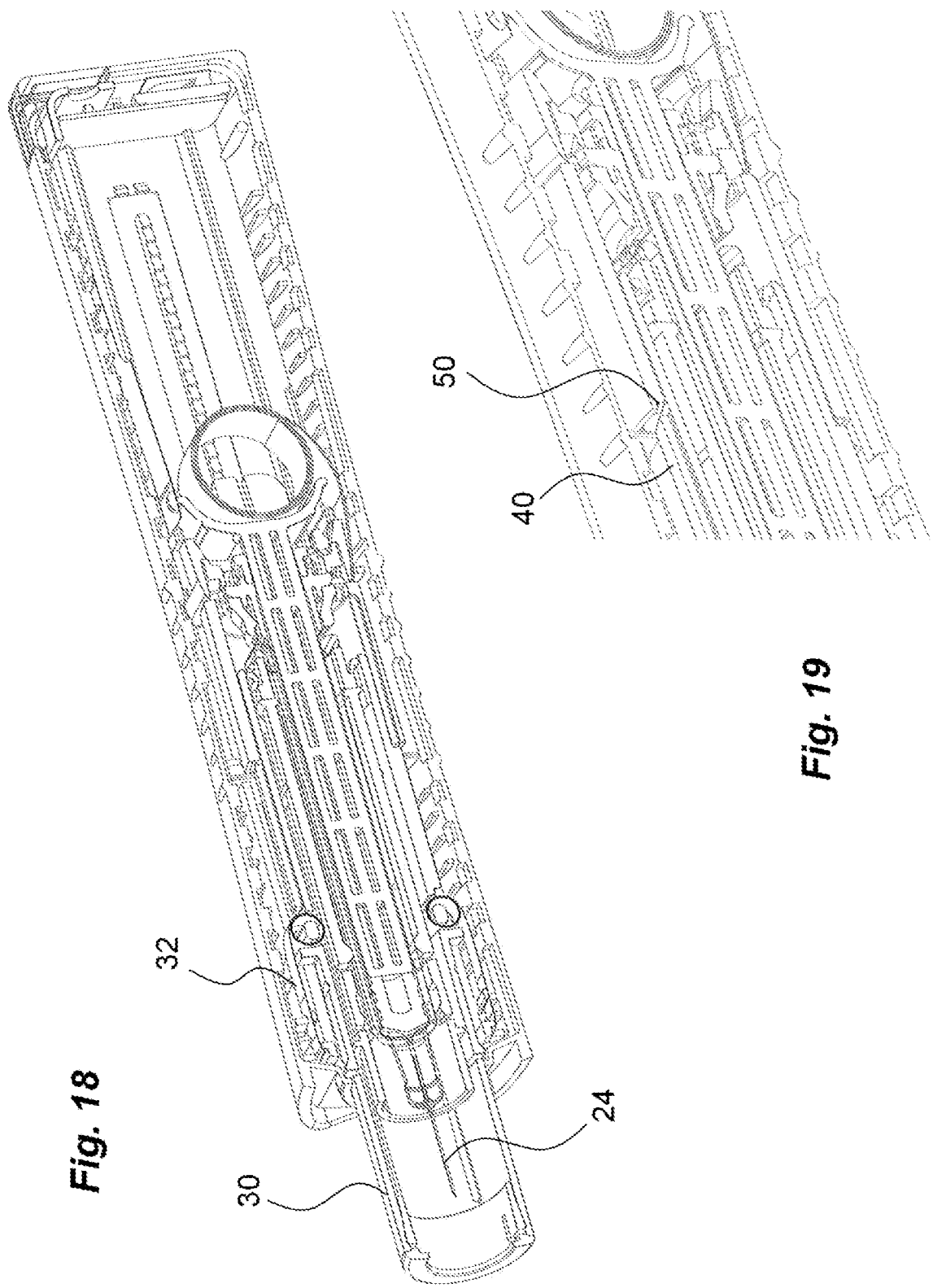

MEDICAMENT DELIVERY DEVICE

CROSS REFERENCE TO RELATED APPLICATIONS

The present application is a U.S. National Phase Application pursuant to 35 U.S.C. § 371 of International Application No. PCT/EP2016/075797 filed Oct. 26, 2016, which claims priority to European Patent Application No. 15195279.3 filed Nov. 19, 2015. The entire disclosure contents of these applications are hereby incorporated by reference into the present application.

TECHNICAL AREA

The present invention relates to a medicament delivery device comprising a number of automatic features.

BACKGROUND OF INVENTION

There is a constant development of medicament delivery devices that are intended and designed to be used and handled by users that are not qualified nursing staff or physicians, i.e. handled by the patients themselves. Because the patients themselves handle the treatment, based on a specific treatment scheme, the physicians treating the patient have no direct information that the treatment schemes are followed as prescribed.

In order to obtain more information regarding the treatment, a number of devices have been developed that are capable of monitoring the dose delivery operations and to store this information. Some devices are also capable of transmitting the information to external storage locations that are accessible to a trained healthcare staff. This enables access to relevant dose delivery information to e.g. a physician of a patient.

Document U.S. Pat. No. 8,361,026 discloses a medicament delivery device that is arranged with a number of intelligent functions that may monitor the operation of the device. Among the functions are monitoring of appliance and/or adherence of the patient and uploading of the information to a suitable storage means of a remote device, where the latter could be a remote communication network, a computer, a smart phone, personal digital assistant, etc. Information could also be downloaded to the medicament delivery device to be accessible to the user, such as if the drug of a medicament in the device has been recalled by the manufacturer of the drug, that the drug has expired or updated user information. In this regard, the device is arranged with a number of switches that are activated during different functional stages.

In order for the device to function it is energized before use by pressing a start button, thus requiring a specific handling step in order to be able to use the device. Further, when the device is energized, its different electronics components and many functions will consume energy. This may be a pronounced drawback if the device is energized but not used directly for some reason. There is further a risk that the start button is operated unintentionally, thereby energizing the device by accident. If the device is to be used at a later stage, the power source of the device may then be depleted.

BRIEF DESCRIPTION OF INVENTION

In the following description, the wording medicament delivery device will be used. In this context, medicament delivery devices may include a number of devices capable of delivering certain doses of medicament to a user, such as e.g. injection devices with or without injection needles, inhalers of all kinds, such as powder, aerosol driven, gas, nebulizers having mouth or nasal pieces, dispensers for medicament in tablet form, eye dispensers, creme/gel dispensers, etc. The medicament delivery devices may be of either disposable type or re-usable type and may be provided with medicament containers suitably arranged for specific drugs in specific forms.

Further, the term "distal part/end" refers to the part/end of the device, or the parts/ends of the members thereof, which under use of the device, is located the furthest away from a delivery site of a patient. Correspondingly, the term "proximal part/end" refers to the part/end of the device, or the parts/ends of the members thereof, which under use of the device is located closest to the delivery site of the patient.

In the following description, the term "smart devices" will be used. In this context, smart devices may include electronic devices that are provided with processors that are capable of running computer programs, as well as comprising storage space to store programs and data retrieved from different external sources. It is further to be understood that the smart devices are provided with communication systems that are capable of communicating with data networks in order to access different databases. It is to be understood that databases may be accessed via the internet, so called cloud services, and/or databases that are connected directly to and accessed via local area networks. It is further to be understood that the smart devices in this context comprise some sort of human-machine interface for two-way communication. The human-machine interface may comprise displays, keyboards, microphones, loudspeakers, I/O-ports for connection of peripherals. Further, the smart devices may be provided with antennas for wireless communication with the networks. Also, the smart devices may be arranged with receiving and transmitting mechanisms capable of communicating with RFID/NFC tags, as well as programs capable of establishing and handling the communication with these tags. It is further to be understood that the smart devices may comprise near range communication technology such as RFID, NFC, Bluetooth, Ant, Zigbee, or the like.

The aim of the present invention is to remedy the drawbacks of state of the art medicament delivery devices. This aim is obtained by a medicament delivery device provided with the features of the independent patent claim. Preferable solutions form the subject of the dependent patent claims.

According to a main aspect of the invention, it comprises a medicament delivery device comprising a housing, wherein the housing may be arranged to accommodate a medicament container (20). Further the medicament delivery device may comprise a power unit comprising a drive force element and an actuation unit operably connected to the drive force element (98). The actuation unit may be movable, upon activation of the drive force element, for expelling a dose of medicament from medicament container.

A monitoring unit may further be provided, that is arranged with an electrical power source for operating the monitoring unit. The medicament delivery device may further comprise an activation element operably connected to the actuation unit, to the monitoring unit and to the electrical power source. Thereby the activation element may be arranged to allow connection between the electrical power source and the monitoring unit when the actuation unit is moved. Thus the monitoring unit will monitor and register the use of the medicament delivery device.

According to one feasible solution, the activation element may comprise a flexible elongated member attached with a first end to the actuation unit and with a second end to the monitoring unit. In this regard, the activation element may be a band and wherein areas of the band are arranged between the power source and electrical connection points of the monitoring unit. Thus, a pure mechanical element is used for activating the power source, creating a contact between e.g. a battery and the leads of the monitoring unit.

According to one solution, the areas of the band arranged between the power source and electrical connection points may be arranged to be pulled away, causing an electrical connection. On the other hand, the band may comprise areas provided with conductive properties, wherein the areas with conductive properties move relative to the power source and the electrical connection points, causing an electrical connection when the actuation unit is moved.

Preferably the connection points may be positioned in a plane with a distance between them, wherein the band may be arranged in the same plane as the connection points, wherein the band may comprise areas provided with a width that is smaller than the distance between the connection points, and wherein the areas with smaller width may be moved between the power source and electrical connection points, causing an electrical connection when the actuation unit is moved.

Further, the monitoring unit may comprise at least one mechanically operated switch element wherein the activation element may be operably connected to the at least one switch element such that the at least one switch element is operated, causing an electrical connection when said actuation unit is moved. Here, instead of connecting the power source directly to the monitoring unit, a switch is operated for activating the monitoring unit. In this respect, the activation element may be releasably attached to the at least one switch element.

According to a further aspect of the invention, the monitoring unit may further comprise a user interface and in that regard, the user interface may comprise visual, audio and/or tactile information elements. Preferably, the monitoring unit may further comprise a communication unit capable of communicating with external information receivers. Here, the communication unit may comprise near-range wireless communication technologies, mobile communication technology and/or WIFI-technology.

According to a further aspect of the invention, it may further comprise a window at a distal area of the housing, wherein the activation element may be arranged to pass the window. This solution provides dual functions of the activation element. In this regard, the activation element may be arranged with indicia on surfaces thereof, which indicia may be visible in the window when the activation element is passing the window when the actuation unit is moved. Preferably the indicia may be arranged to create a moving impression when said activation element is passing said window.

According to a further aspect, the monitoring unit may be positioned at a distal end of the housing adjacent the window. Regarding this, the monitoring unit may be arranged with a number of light sources, which light sources are visible through the window when the monitoring unit is activated. Hereby, the light sources may be capable of emitting light of different colour/intensity/blinking frequency.

These and other aspects of, and advantages with, the present invention will become apparent from the following detailed description of the invention and from the accompanying drawings.

BRIEF DESCRIPTION OF DRAWINGS

In the following detailed description of the invention, reference will be made to the accompanying drawings, of which

DETAILED DESCRIPTION OF THE INVENTION

Figure 1:
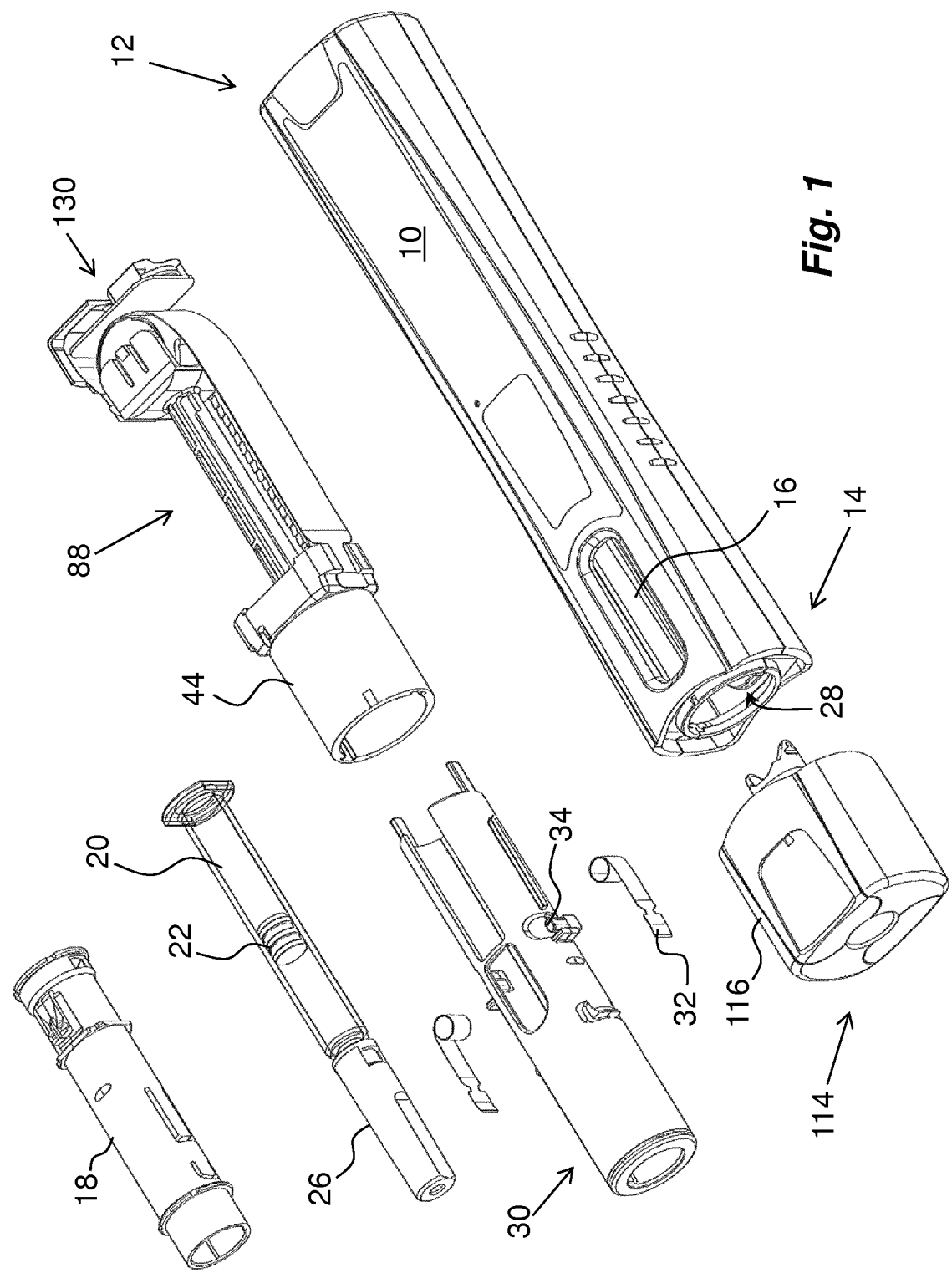
FIG. 1 shows an exploded view of one embodiment of a medicament delivery device.

The medicament delivery device shown in the drawings comprises an outer housing 10 with a generally tubular shape, having a distal end 12 and a proximal end 14. The housing 10 may comprise a number of housing parts, such as two housing parts as shown in the embodiment of FIG. 1. It is to be understood that the housing may have fewer or more housing parts depending on manufacturing and/or assembly methods.

The proximal part of the housing 10 is further arranged with openings or windows 16. A medicament container holder 18 is arranged to accommodate a generally tubular elongated medicament container 20 provided with a movable stopper 22 and arranged with a medicament delivery member 24 that in the embodiment shown is an injection needle, FIG. 2. It is however to be understood that other types of medicament delivery members such as nebulizers, mouth or nose pieces may be used, just to mention a few. The medicament delivery member 24 may be integrated with the medicament container 20 or may be an attachable part that may be connectable in many ways such as with threads, bayonet couplings, luer connections, and the like.

The medicament delivery member 24 is further surrounded by a removable medicament delivery member shield 26 that in the embodiment shown is in the form of a so called rigid needle shield 26 (RNS). It is however to be understood that other types of medicament delivery member shields such as so called flexible needle shields (FNS) may be used instead.

The proximal end of the housing 10 is arranged with a central passage 28 through which a generally tubular medicament delivery member guard 30 can protrude. The medicament delivery member guard 30 is urged in the proximal direction by two medicament delivery member guard resilient elements 32 in the form of at least one flat spiral spring spring, which is arranged with a free end attached to the interior of the housing and with the wound part around a post 34 on the medicament delivery member guard 30, FIG. 1. The medicament delivery member guard 30 is provided with a proximal, generally tubular part 36 provided with a central passage 35, FIG. 3. At the distal end of the tubular part 36, cut-outs 37 are arranged, providing two sections 38 extending in the distal direction. Each section 38 is arranged with a distally directed arm 39, the function of which will be described below.

Figure 3:
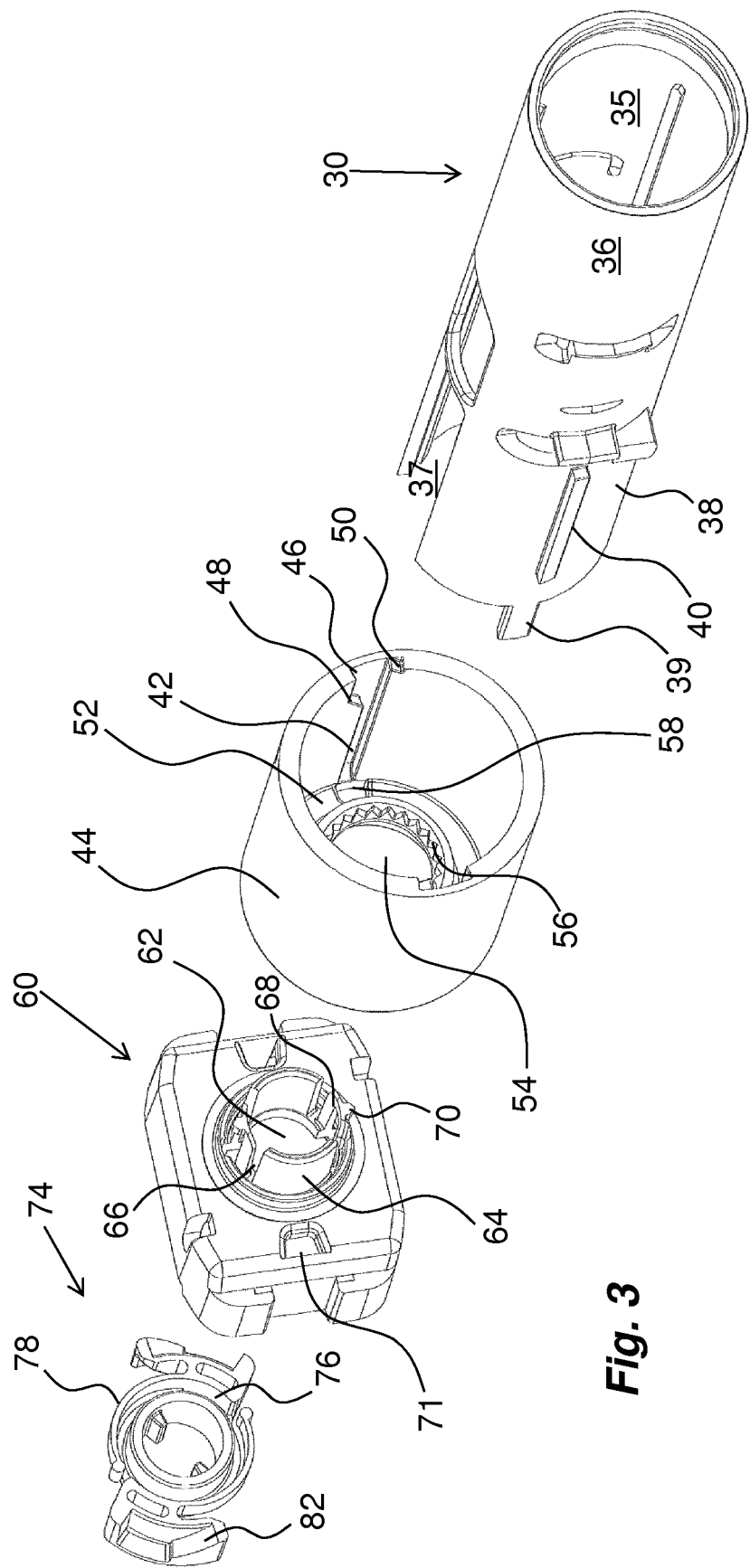

Further, the outer surfaces of the sections 38 are each arranged with rotator activator elements that in the embodiment shown are in the form of longitudinally extending ridges 40, FIG. 3. The ridges 40 are arranged to cooperate with guide elements in the form of longitudinal grooves 42 on an inner surface of a generally tubular rotator 44. At the proximal end of the grooves 42 a cut-out 46 is arranged, having a longitudinally extending side wall which transforms into an inclined surface 48 connecting to the longitudinal groove 42. Further on the opposite side of the longitudinal groove as seen in the circumferential direction, a seat 50 is arranged, the function of which will be described below.

The rotator 44 is further arranged with a transversal wall 52, which wall 52 is arranged with a central passage 54, FIG. 3. The edge of the central passage 54 is arranged with a circumferential ratchet 56. Further the transversal wall 52 is arranged with a number of through-holes 58 between the central passage 54 and the inner surface of the rotator 44, through which the arms 39 of the medicament delivery member guard 30 may protrude, as will be described below.

Figure 4:
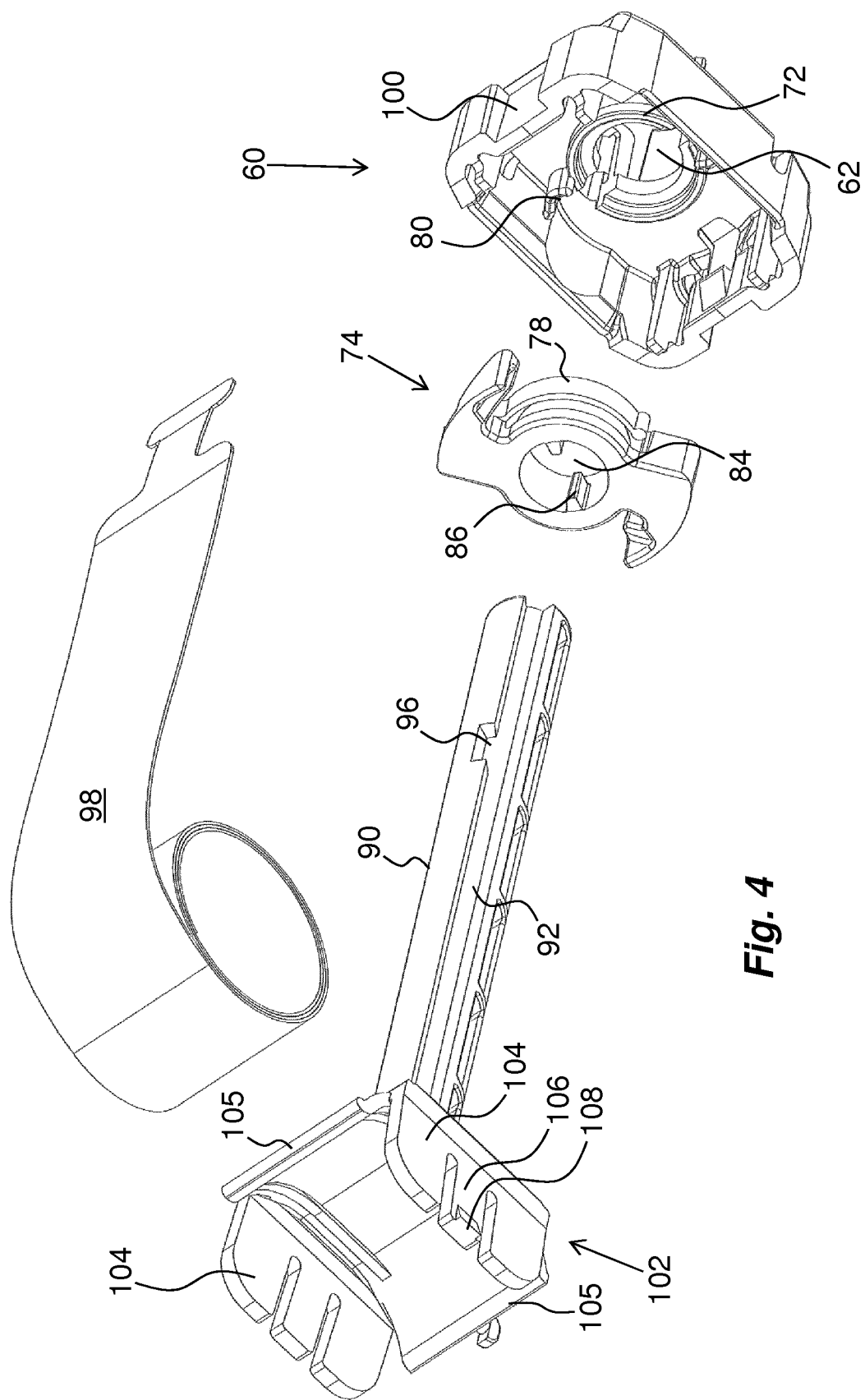

A latch carrier 60 is further arranged distal of and adjacent the rotator 44, FIGS. 3 and 4. The latch carrier 60 is attached to the housing and is arranged with a central passage 62. The central passage 62 is arranged with a generally tubular element 64 extending in the proximal direction and into the central passage of the rotator 44. The tubular element 64 is further arranged with longitudinal cut-outs 66 whereby tongues 68 are formed between the cut-outs 66. The tongues 68 are flexible in the generally radial direction and are arranged with outwardly directed protrusions 70 that are to engage with and cooperate with the ratchet 56 of the rotator 44. Thereby the protrusions 70 are configured to mate with the ratchet 56. The latch carrier 60 is further arranged with two through-holes 71, through which the arms 39 of the medicament delivery member guard 30 may protrude, as will be described below.

The distally directed surface of the latch carrier 60 is arranged with a circular seat 72 that surrounds the central passage 62, FIG. 4. A release clip element 74 is arranged with a circular groove 76 in which the circular seat 72 fits so that the release clip element 74 is rotatable in relation to the latch carrier 60. The release clip element 74 is further arranged with flexible arms 78, having free ends that fit into seats 80 of the latch carrier 60. The release clip element 74 also comprises activation surfaces in the form of two proximally directed ridges 82 having a wedge-shaped form as seen in a longitudinal cross-section. The wedge-shaped ridges 82 are positioned generally adjacent the through-holes 71 of the latch carrier 60. The release clip element 74 is arranged with a central passage 84, FIG. 4, which central passage 84 is arranged with radially inwardly directed ledges 86.

The medicament delivery device is further arranged with a power unit 88, FIG. 1. The power unit 88 features an actuation unit that comprises an elongated plunger rod 90 that extends through the rotator 44, the latch member 60 and the release clip element 74, FIG. 2. The plunger rod 90 is arranged with two longitudinal grooves 92 arranged on opposite sides, as shown in FIGS. 4 and 5, which grooves 92 each are arranged with two cut-outs 94, 96, one cut-out 94 at a distal end of the plunger rod 90 and one cut-out 96 in the proximal area, FIG. 6. The plunger rod 90 is arranged to cooperate with the inwardly extending ledges 86 of the central passage 84 of the release clip element 74, which ledges 86 fit into the longitudinal grooves 92 of the plunger rod 90. The ledges 86 will also co-act with the cut-outs 94, 96 as will be explained.

The power unit 88 further comprises a drive force element 98 that in the embodiment shown comprises a flat spiral spring, FIGS. 4 and 6, which is arranged to provide a driving force that moves the actuation unit 88 proximally to move the stopper 22 within the medicament container 20 to dispense medicament from a medicament delivery member 30. One end of the drive force element 98, i.e., a proximal end, is attached to the latch carrier 60 through a connecting element 100, FIG. 4. The distal end of the drive force element 98 is coiled and placed in a seat 102 comprised in the actuation unit 88. The seat is attached to, or made integral with, a distal end of the plunger rod 90. The seat 102 is arranged with side walls 104 and generally arc-shaped end walls 105 to accommodate the drive force element 98. The drive force element 98 is preferably a variable force spring or a constant force spring and is not a traditional helical compression spring made from a helix of wire. The side walls 104 are further arranged with cut-outs so as to form flexible tongues 106. The free ends of the tongues 106 are arranged with outwardly directed wedge-shaped protrusions 108, which wedge-shaped protrusions 108 are arranged to interact with wedge-shaped teeth 110 on brackets 112, FIG. 6, on each side of the seat, which brackets 112 are fixedly attached to the housing, the function of which will be described below.

Figure 2:
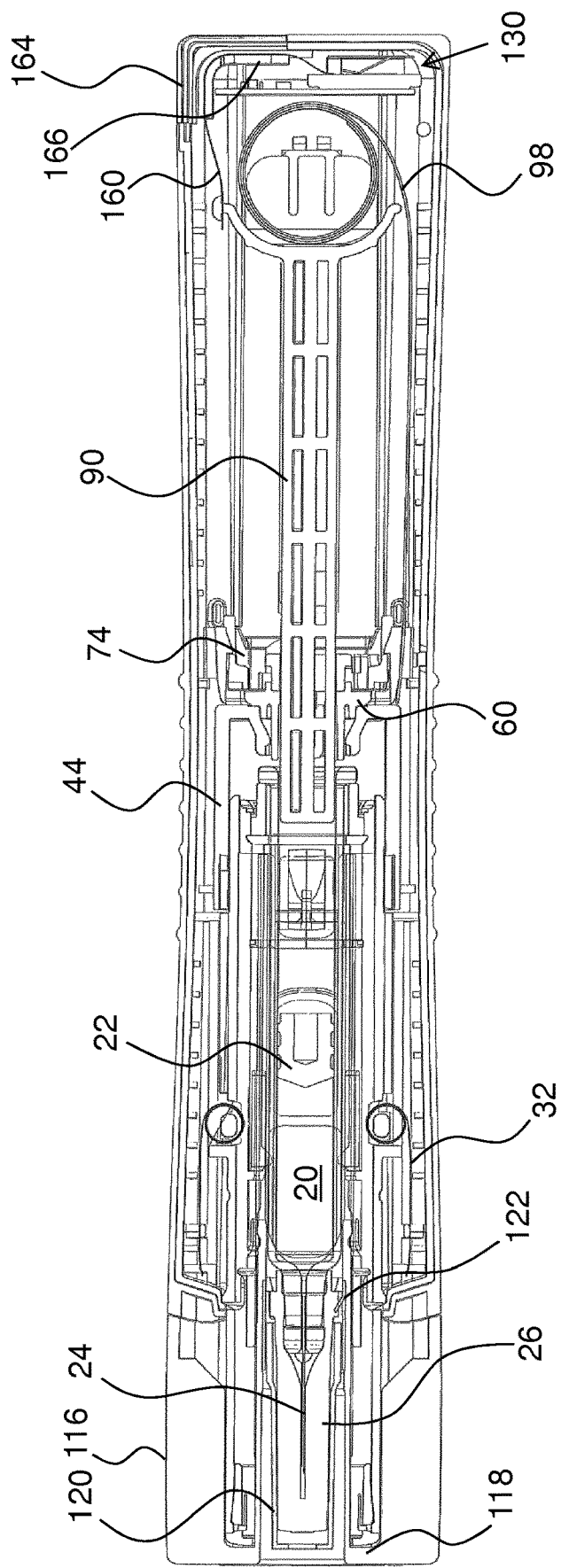
FIG. 2 shows a cross-sectional view of the medicament delivery device of FIG. 1, and FIGS. 3-6 show detailed views of components and sub-assemblies comprised in the medicament delivery device of FIG. 1, FIGS. 7-8 show one embodiment of a monitoring unit that may be used with the medicament delivery device according to FIG. 1, FIGS. 9-11 and 18-19 show partly cross-sectional views of different functional states of the medicament delivery device of FIG. 1, and FIGS. 12-17 show different functional states of the monitoring unit of FIG. 7.

The medicament delivery device further comprises a medicament delivery member shield remover 114, FIGS. 1 and 2. It comprises a generally tubular grip part 116 having an end wall 118. The distally directed surface of the end wall 118 is arranged with a seat in which a generally tubular grip element 120 is placed. The grip element 120 will be coaxial with and surrounding the medicament delivery member shield 26 when the medicament delivery member shield remover 114 is attached to the proximal end of the medicament delivery device. The grip element 120 comprises a number of generally proximally directed somewhat inwardly inclined tongues 122 that are engaging the outer surface of the medicament delivery member shield 26.

Figures 7A, 7B:
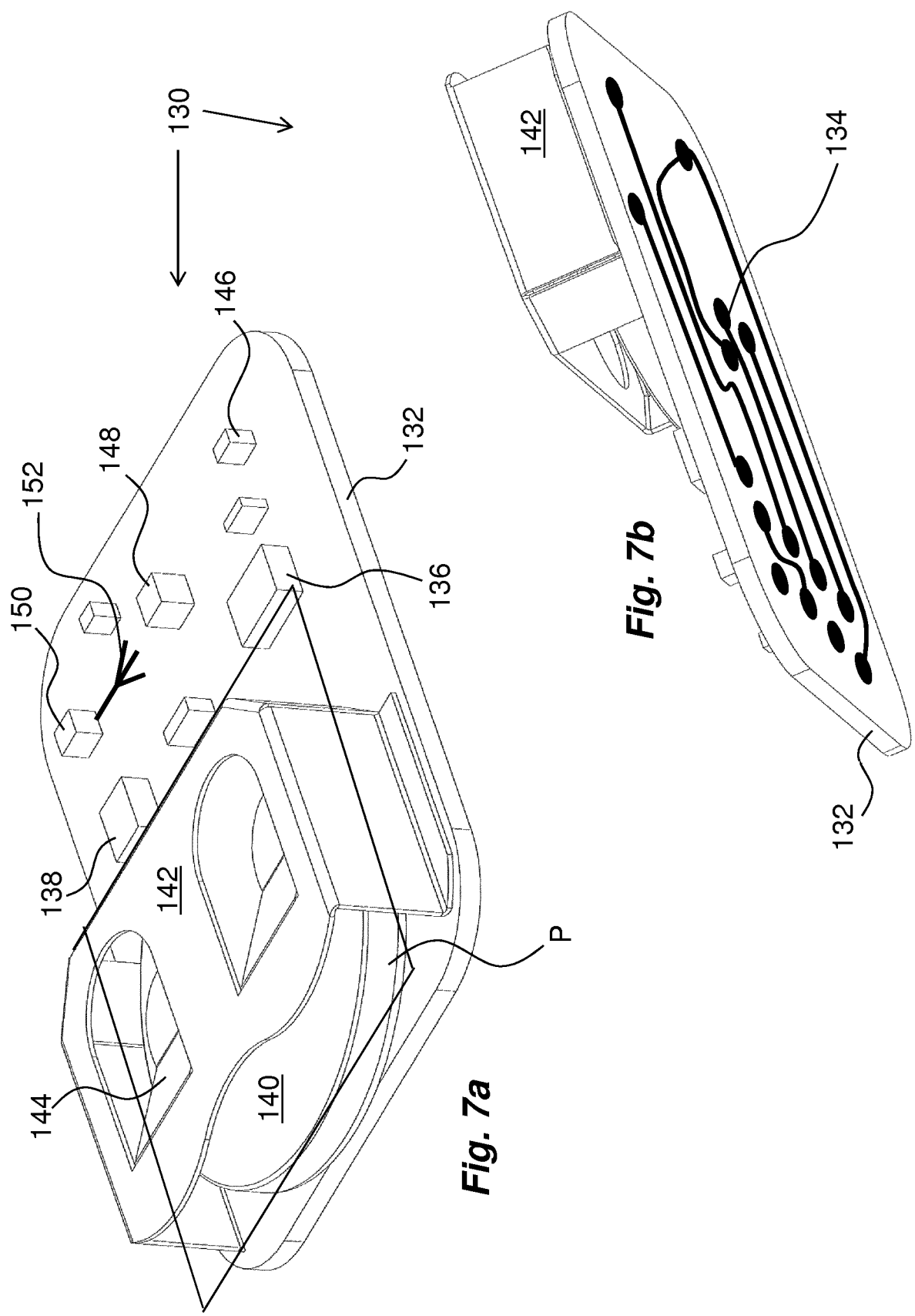

According to the present invention, a monitoring unit 130 is arranged to the medicament delivery device, FIGS. 1 and 7. It comprises a printed circuit board PCB 132 placed at the distal end of the medicament delivery device. The PCB 132 is arranged with an electronic circuit 134 provided with a number of functions and elements depending on the desired functionality of the monitoring unit. The electronic circuit may comprise a processor 136 as well as data storage elements 138. Preferably the monitoring unit 130 is arranged with a power source such as a battery, 140, preferably a small button cell as well as electric connection elements 142 that may comprise flexible tongues 144 providing connection points that are pressing against the poles of the battery 140. As seen in FIG. 7*a*, the electric connection points are placed in a plane P coinciding with the upper surface of the battery 140. The monitoring unit 130 is further arranged with a user interface, which may be capable of communicating in different ways with a user. This could for example comprise audio elements 146 that could produce audio signals indicating different status conditions of the medicament delivery device.

In addition or as an alternative, the monitoring unit may comprise visual elements 148 that are capable of providing visual information to a user, such as lights, displays and the like. The lights may further comprise light sources capable of emitting light of different colour/intensity/blinking frequency, for instance. Further, the monitoring unit may be arranged with wireless communication units 150. These may include near range wireless transmission technologies such as RFID, NFC, Zigbee, Ant, Bluetooth, for example. The communication units 150 may also comprise wireless transmission technologies that work on longer ranges such as radio transmission, GSM, 4G, 5G, WIFI, etc. In this respect, the communication units 150 comprise appropriate antenna elements 152.

According to a possible feature, if the monitoring unit 130 is provided with communication circuits, then monitored data obtained by the monitoring unit may be transferred to external storage sources and/or external devices. If for instance NFC technology is used, then a mobile NFC-enabled smart device may derive the monitored data from the usage management module. The same functionality may also be provided when using Bluetooth communication technologies.

The smart device may then either be capable of processing the data, such as e.g. calculating the time and date of an occurrence of the medicament delivery device, or may in turn transmit the monitored data to external databases via the communication technologies of the mobile device, such as cellular radio communication networks, e.g. GSM, 3G, 4G, etc. and/or wireless local area networks, which networks can provide access to the internet and thus to a large number of external data storage sources, data handling centres, etc.

Regarding communication technologies, it is of course possible to incorporate the above mentioned communication technologies in the monitoring unit 130 as such. Then the monitoring unit may communicate directly with external data storage sources, data handling centres etc. via the communication networks. The monitored data may preferably be accessible to a physician or the like skilled person who is responsible for the treatment of the user of the medicament delivery device and who might have prescribed a treatment scheme. This retrieved monitored data may then be evaluated to derive information such as adherence, and the lack of which may lead to measures from the physician.

The electronic circuit 134 of the monitoring unit 130 may further be arranged with a positioning function whereby the geographical position of the user may be obtained and used for different purposes. In this respect, the positioning may be obtained by different functions. Either the electronics circuit is provided with a GPS-module, whereby the actual position of the user when the dose is delivered is recorded by GPS coordinates. Another possibility is to use the GSM-function for locating the position. The GPS-function and the GSM-function may further be combined with a WIFI location function for improved indoors location.

Figure 8:
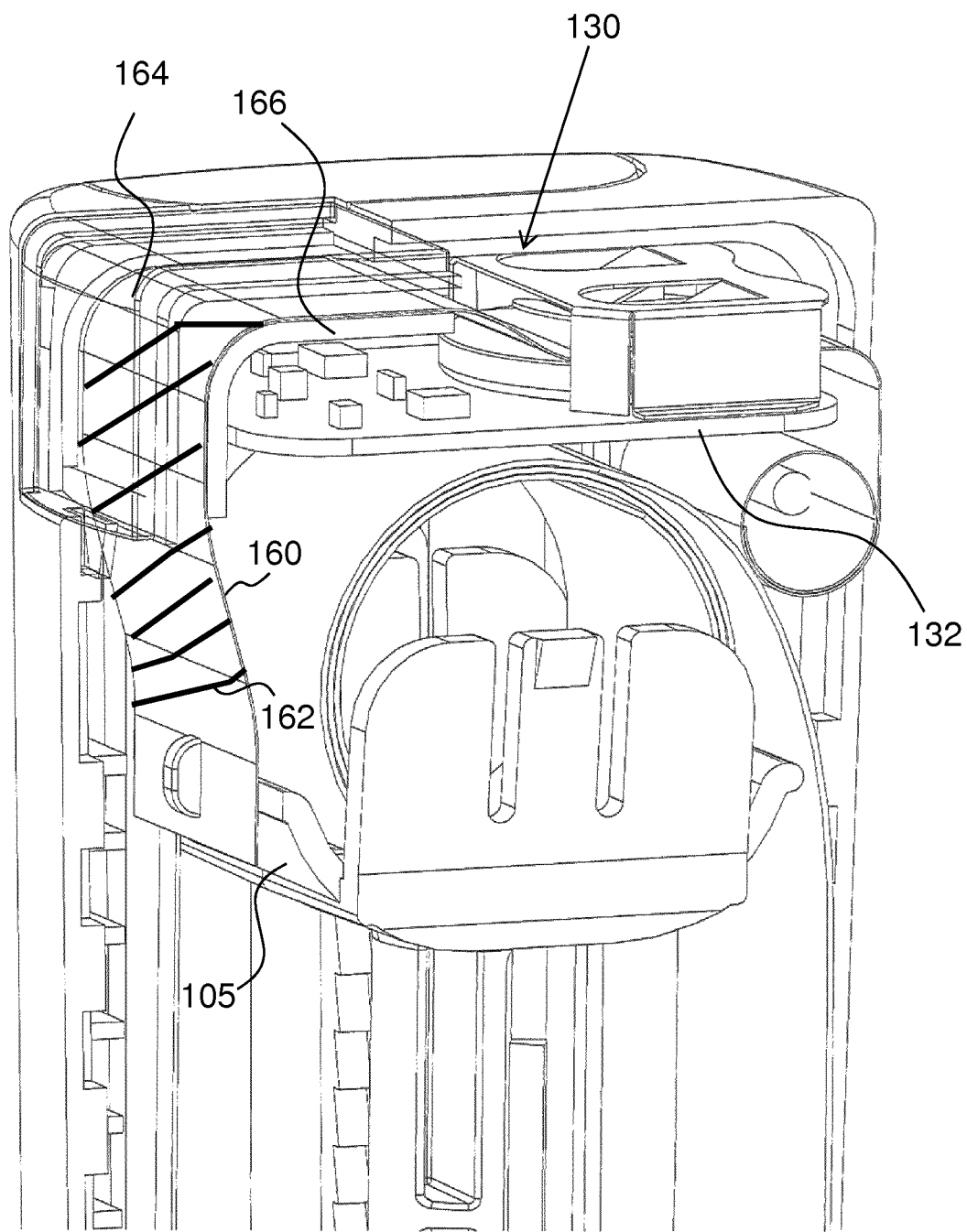

In order to activate the monitoring unit, an activation element 160 is arranged in the medicament delivery device. In a preferred embodiment, the activation element 160 is operably connected to the monitoring unit and according to one embodiment shown in FIG. 8, the activation element 160 comprises a flexible elongated member such as a ribbon or a band, or the like, where one first end of the activation element 160 is attached to the actuation unit and in particular to the outer surface of one of the arc-shaped end walls 105 of the seat as seen in FIG. 8. The other second end of the activation element 160 is arranged to the monitoring unit as will be described below.

The activation element 160 may be arranged with indicia 162 on a side surface. Further the housing may be arranged with an opening or window 164 at its distal end, FIG. 2, which window 164 preferably may be arranged with a transparent material, and possibly also with magnifying properties. A guide surface 166 is arranged in connection with the window, on which the band 160 may be supported as will be described.

The device is intended to function as follows. When the medicament delivery device is delivered to a user, a medicament container 20 with an attached medicament delivery member shield 26 has been placed in the medicament container holder 18 and a medicament delivery member shield remover 114 has been attached to the proximal end of the medicament delivery device. The drive force element 98 has been tensioned in that the plunger rod 90 has been pushed distally relative the release clip element 74 such that the inwardly directed ledges 86 in the central passage 84 of the release clip element 74 engage with the proximally positioned cut-outs 96 of the plunger rod 90, thereby holding the plunger rod 90 in a tensioned state. The release clip element 74 is urged and held in this position by the flexible arms 78 of the release clip element 74 resting in the seats 80 of the latch carrier 60.

When the medicament delivery device is to be used, the proximal end of the medicament delivery member guard 30 is pressed against a dose delivery site. This causes the medicament delivery member guard 30 to move distally relative to the rest of the medicament delivery device. The ridges 40 on the outer surface of the sections 38 of the medicament delivery member guard 30 will come in contact with the inclined surface 48 of the grooves 42 of the rotator 44, FIG. 9, thereby turning the rotator 44. As the rotator 44 is forced to rotate, the circumferential ratchet teeth 56 move out of engagement with the protrusions 70 on the flexible arms 68 of the latch carrier 60. This first rotation of the rotator 44 is not large enough to fully index the protrusions 70 into an adjacent ratchet tooth. This less than-full-indexing, i.e., partial indexing, imparts a second biasing force on the rotator 44 as a result of the flexible teeth 70 urging the rotator 44 to continue in rotation in the direction of the first slight rotation caused by the first biasing force imparted by ridge 40. This second biasing force remains as ridge 40 travels proximally and then distally in groove 42.

Further, as the medicament delivery member guard 30 is moved in the distal direction, the arms 39 will enter the through-holes 58 of the rotator 44 as well as the through-holes 71 of the latch carrier 60 whereby the distal ends of the arms 39 will engage with and press on the inclined surfaces of the wedge-shaped ridges 82 of the release clip element 74. This action will cause the release clip element 74 to turn against the force of the flexible arms 78, wherein the turning of the release clip element 74 will cause the inwardly directed ledges 86 of the release clip element 74 to move out of the cut-outs 96 of the plunger rod 90.

The plunger rod 90 is now free to move and will be forced in the proximal direction by the force of the drive force element 98. The proximal end of the plunger rod 90 will act on the stopper 22, moving it in the proximal direction, thereby expelling a dose of medicament through the medicament delivery member 24. Since the plunger rod 90 is moving in the proximal direction, so is the seat 102 with the wedge-shaped protrusions 108, wherein the protrusions 108 will move along and in contact with the wedge-shaped teeth 110 of the brackets 112, causing audible and tactile information that a dose delivery sequence is performed, FIG. 11.

Further, according to one feasible solution, a second free end of the activation element 160 is of a generally non-conductive and electrically insulating material and is arranged between the poles of the battery 140 and the contact points of the resilient connection elements 142 of the monitoring unit 130, thereby insulating the battery 140 from the electronic circuit 134. Thus as seen, the band 160 is in the same plane P as the contact points. The movement of the plunger rod 90 with the seat 102 will pull the activation element 160 so that it is removed from the battery 140, wherein the battery 140 is connected to the electric circuit 134 of the monitoring unit 130 via the contact points of the flexible tongues 144, activating the monitoring unit 130. According to the design of the activation element shown in FIG. 12, the band 160 is long, maybe curled in a roll 168, and arranged with indicia 162 on its surface. During the dose delivery sequence the activation element will move past the window 164 such that the indicia 162 is visible, whereby the pattern of the indicia gives a visual indication that the dose delivery sequence is performed. As the band is pulled, it passes between the connection elements and the battery, keeping the monitoring unit inactivated since it is electrically insulating. At or near the end of the dose delivery sequence the band 160 is pulled away from the battery 140.

Thus, with this solution having a long band 160, the monitoring unit 130 is activated at or near the end of the dose delivery sequence. It is to be understood that the band may have a length such it is pulled away at any position during the dose delivery sequence. The injection sequence is ended when the inwardly directed ledges 86 of the release clip 74 reach the distal end of the longitudinal groove 92 of the plunger rod 90, whereby the release clip 74 will be turned by the flexible arms 78 such that the inwardly directed ledges 86 fit into the distal cut-outs 94 of the plunger rod 90.

Figure 12:
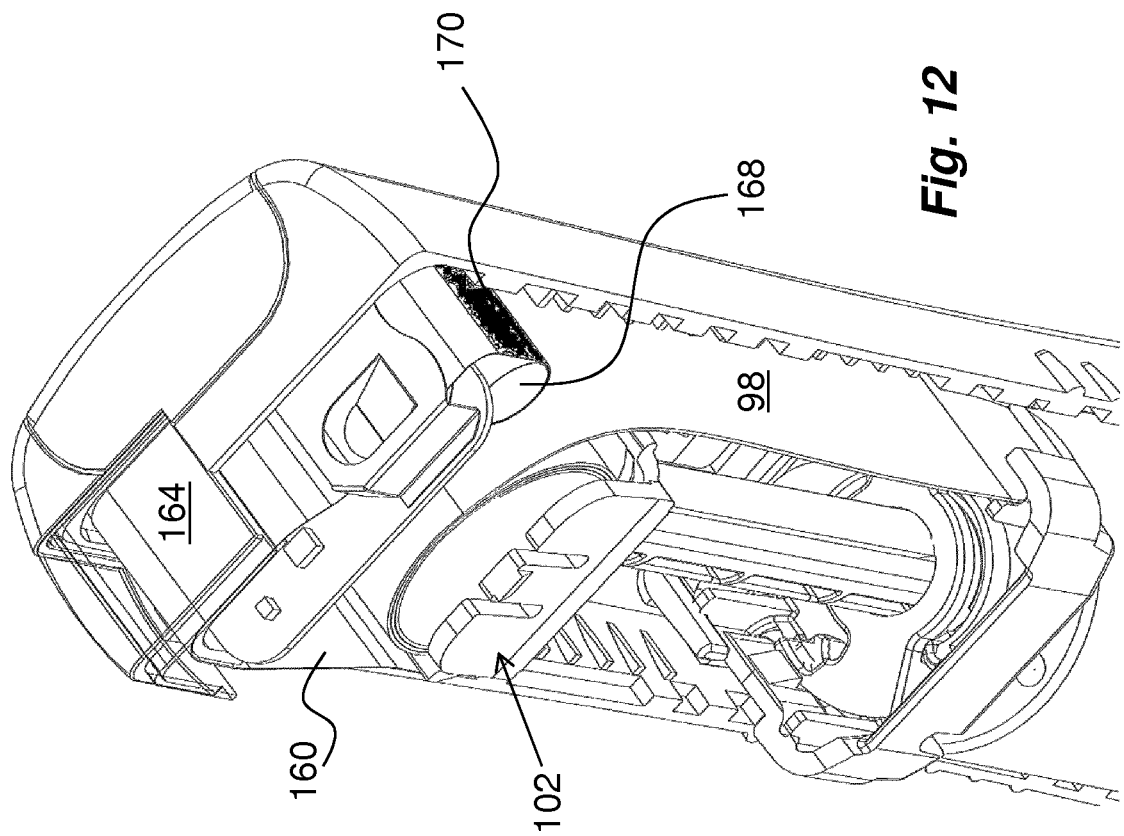

If it is desired that the activation is performed earlier during the dose delivery sequence, at the start or during the dose delivery sequence, the band of the activation element may be arranged with areas with conductive material 170 along the length of the band 160, FIG. 12, such that the conductive material 170 will cause an electrical connection of the battery 140 to the electronics circuit 134 of the monitoring unit 130. At the same time, the indicia 162 on the activation element 160 are shown in the window 164. Preferably the indicia 162 are arranged to create a moving impression when the band 160 is passing the window 164.

Figure 13:
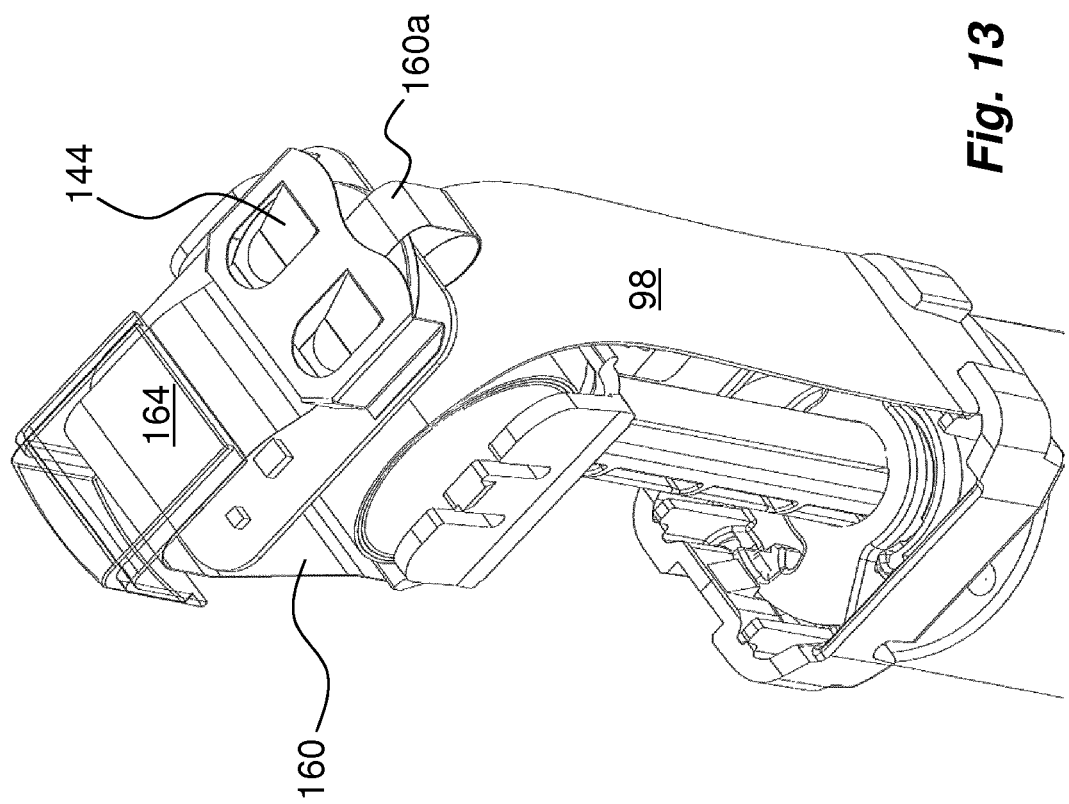

Another solution is shown in FIG. 13 where the activation element 160 has a smaller width, which smaller width is chosen to be less than the distance between the contact points, at a certain length 160a, thereby providing a removal of the activation element 160 from the battery poles and the contact points and an activation of the monitoring unit at the same time as the band 160 continues to pass the window 164 and between the contact points.

Figure 15:
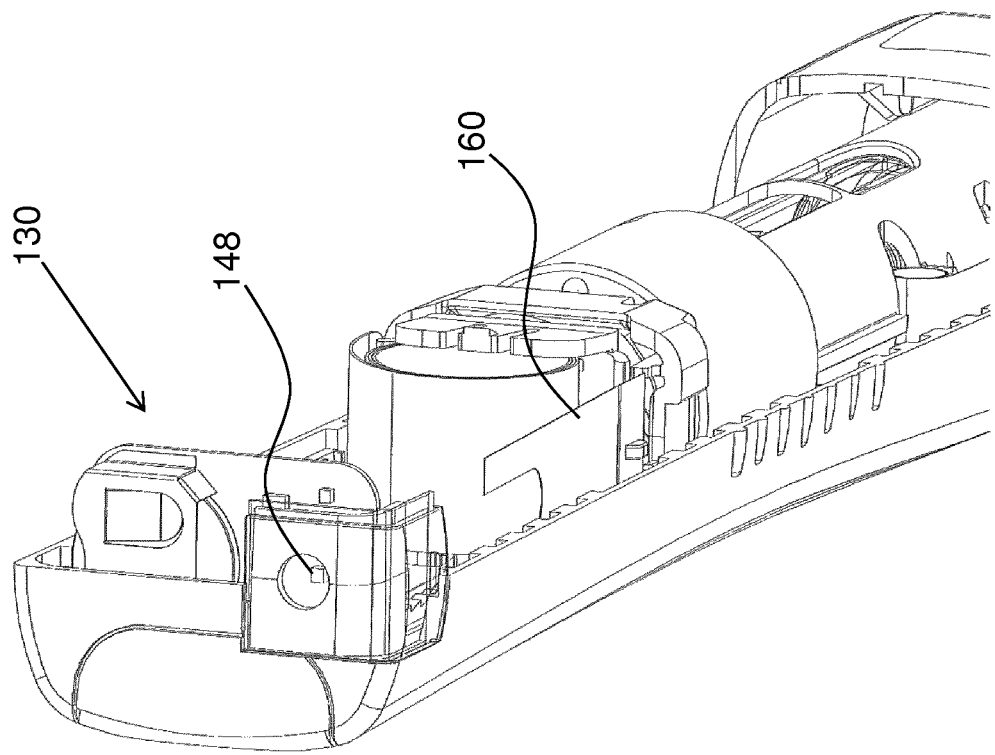
Figure 14:
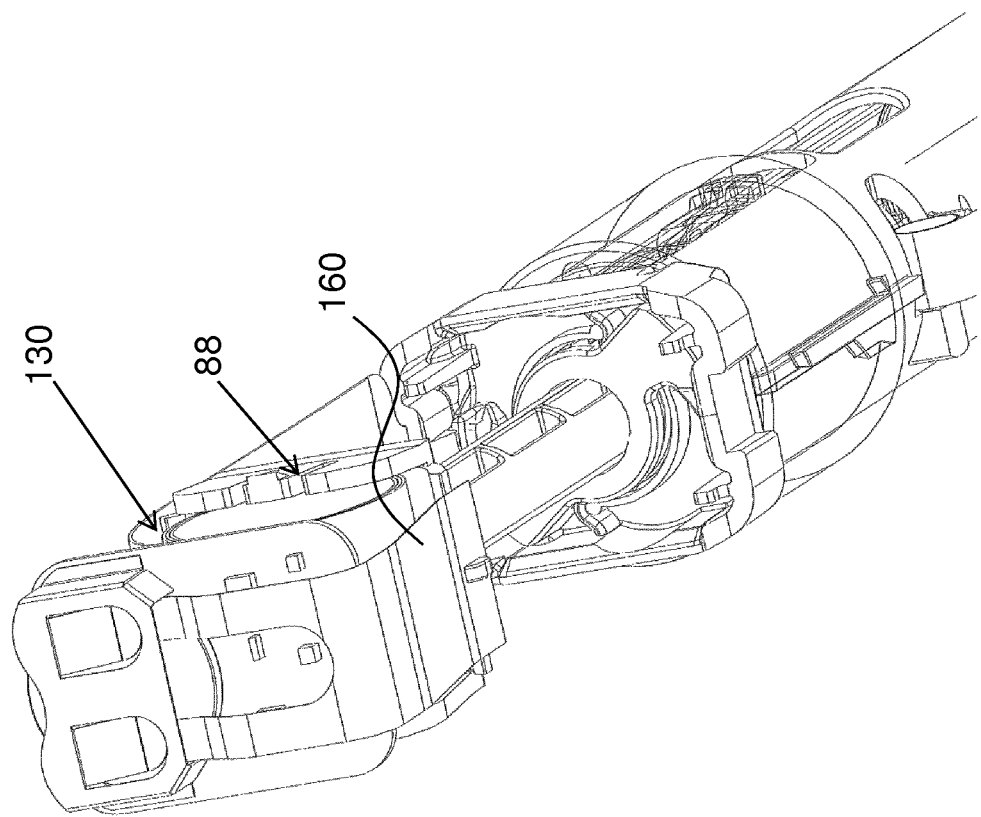

According to a further solution shown in FIGS. 14 and 15, the activation element is a short band 160 that is pulled by the power unit 88. In this solution, the monitoring unit 130 is activated at the beginning or during the dose delivery sequence and not at the end. In this solution, there is no visual indication by indicia on the band 160 during the dose delivery sequence, which may not be necessary or which may be obtained by the visual element 148, FIG. 15, that for example may be a light source on the monitoring unit that is activated when the monitoring unit has been activated. The light source can be flashing during the dose delivery sequence or may be red during the dose delivery sequence and switching to green when it is safe to remove the medicament delivery device. As understood from the above, the starting point may be chosen by modifying the length or the width of the band of the activation element, or by using different conductive areas along the band.

Figure 17:
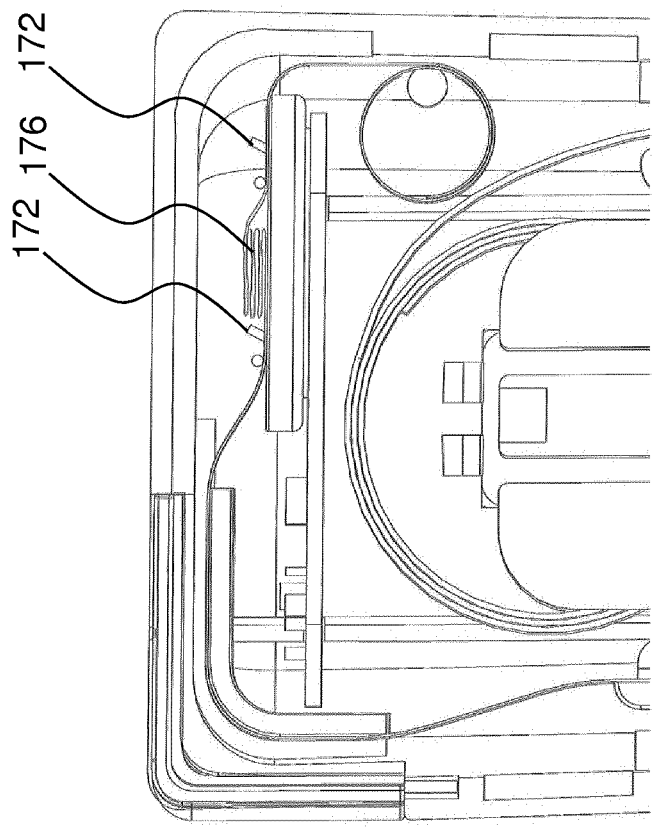
Figure 16:
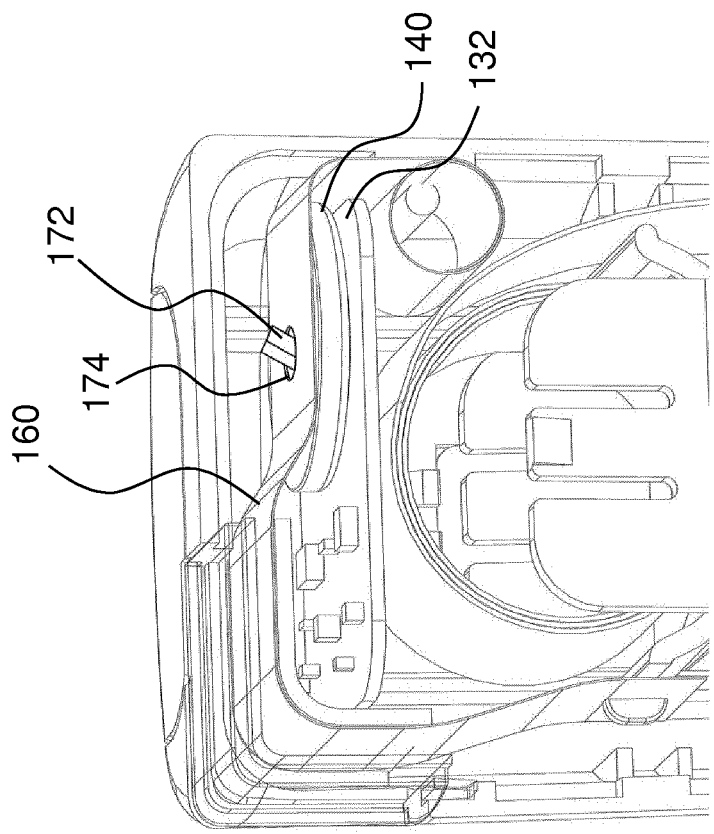

FIGS. 16 and 17 show a further embodiment of the present invention. Here the activation element 160 is operably connected to switches 172 on the PCB 132 of the monitoring unit 130. Thus, the activation element will mechanically affect the switches 172 to connect the battery 140 to the electronic circuit 134. The activation element may either be attached to a free end of the mechanical switch 172, such as an arm, wherein the activation element is removed from the mechanical switch 172 after the switching action, if for example the monitoring unit 130 is to be activated during a dose delivery sequence. On the other hand, the mechanical switch 172 may be operated at the end of the dose delivery sequence whereby it is not necessary that the band 160 is removed from the switch 172.

A further solution may be that the band 160 of the activation element may be arranged with a hole 174 through which the mechanical switch 172 extend, where the whole band 160, or areas around the hole 174, being of such a sturdy material that when the band 160 is pulled, the mechanical switch 172 is operated. Further the activation element 160 may be arranged to operably affect more than one mechanical switch 172, FIG. 17. For instance the band of the activation element may be arranged with a number of holes through which the mechanical switches extend. The band may then be stored or folded, 176, such that it is unfolded and extended successively as the band 160 is pulled during the dose delivery sequence. With this solution a number of switches may be affected at different times during the dose delivery sequence if the band is arranged with a number of holes along its length.

When the dose has been delivered the medicament delivery device is removed from the site. This in turn will cause the medicament delivery member guard 30 to be moved in the proximal direction by the medicament delivery member guard resilient elements 32, extending through the proximal end 14 of the medicament delivery device and covering the medicament delivery member 24, FIG. 18.

When the ridge 40 of the medicament delivery member guard 30 disengages from the groove 42, when the medicament delivery member guard 30 is allowed to fully extend out of the housing 10, the second biasing force causes the rotator 44 to complete the second slight rotation such that the proximal end of the ridge 40 of the medicament delivery member guard 30 is placed in axial alignment with seat 50 of the rotator 44, FIG. 19. This second rotation of the rotator 44 thus completes the formation of the irreversible lockout of the medicament delivery member guard 30. The device can now be discarded in a safe manner.

It is to be understood that the embodiment described above and shown in the drawings is to be regarded only as a non-limiting example of the invention and that it may be modified in many ways within the scope of the patent claims.

The invention claimed is:

1. A medicament delivery device comprising:
a housing arranged to accommodate a medicament container;
a power unit comprising:
a drive force element, and
an actuation unit operably connected to said drive force element, wherein said actuation unit is movable upon activation of said drive force element, to thereby expel a dose of a medicament from said medicament container;
a monitoring unit provided with an electrical power source for operating said monitoring unit; and
an activation element operably connected to said actuation unit, to said monitoring unit, and to said electrical power source, wherein said activation element comprises a flexible elongated member attached with a first end to said actuation unit and with a second end to said monitoring unit, wherein a non-conductive and electrically insulating material of the activation element is arranged between the power source and electrical connection points of said monitoring unit to thereby prevent an electrical connection between said electric power source and said monitoring unit prior to a dose delivery sequence, and wherein at least a portion of said activation element moves with respect to said electrical power source during the dose delivery sequence to thereby enable the electrical connection between said electrical power source and said monitoring unit when said actuation unit is moved.

2. The medicament delivery device according to claim 1, wherein said activation element is a band and wherein non-conductive and electrically insulating material of the band is arranged between the power source and the electrical connection points of said monitoring unit.

3. The medicament delivery device according to claim 2, wherein the non-conductive and electrically insulating material of the band arranged between the power source and the electrical connection points are arranged to be pulled away, causing the electrical connection.

4. The medicament delivery device according to claim 2, wherein the band comprises material areas provided with conductive properties, wherein said material with conductive properties move relative to the power source and the electrical connection points, causing the electrical connection when said actuation unit is moved.

5. The medicament delivery device according to claim 2, wherein said electrical connection points are positioned in a plane (P) with a distance between them, that the band is arranged in the same plane as the electrical connection points, wherein the band comprises areas provided with a width that is smaller than the distance between the electrical connection points, wherein said areas with smaller width are moved between the power source and the electrical connection points, causing an electrical connection when said actuation unit is moved.

6. The medicament delivery device according to claim 1, wherein said monitoring unit comprises at least one mechanically operated switch element, that said activation element is operably connected to said at least one switch element such that said at least one switch element is operated, causing an electrical connection with said actuation unit.

7. The medicament delivery device according to claim 6, wherein said activation element is releasably attached to said at least one switch element.

8. The medicament delivery device according to claim 1, wherein said monitoring unit further comprises a user interface.

9. The medicament delivery device according to claim 8, wherein said user interface comprises visual, audio and/or tactile information elements.

10. The medicament delivery device according to claim 1, wherein said monitoring unit further comprises a communication unit capable of communication with external information receivers.

11. The medicament delivery device according to claim 10, wherein said communication unit comprises near-range wireless communication technologies.

12. The medicament delivery device according to claim 10, wherein said communication unit comprises mobile communication technology and/or WIFI-technology.

13. The medicament delivery device according to claim 1, further comprising a window at a distal area of the housing.

14. The medicament delivery device according to claim 13, wherein said activation element is arranged to pass said window.

15. The medicament delivery device according to claim 14, further comprising a guide surface arranged to guide said activation element past said window.

16. The medicament delivery device according to claim 13, wherein said activation element is arranged with indicia on surfaces thereof, which indicia is visible in said window when said actuation unit is moved.

17. The medicament delivery device according to claim 16, wherein said indicia is arranged to create a moving impression when said activation element is passing said window.

18. The medicament delivery device according to claim 13, wherein said monitoring unit is positioned at a distal end of the housing adjacent said window.

19. The medicament delivery device according to claim 18, wherein said monitoring unit is arranged with a number of light sources, which light sources are visible through said window when said monitoring unit is activated.

20. The medicament delivery device according to claim 19, wherein said light sources are capable of emitting light of different colour/intensity/blinking frequency.

* * * * *